United States Patent [19]

Ammeraal

[11] Patent Number: 5,229,370
[45] Date of Patent: Jul. 20, 1993

[54] WATER SOLUBLE BRANCHED BETA CYCLODEXTRIN STEROID COMPLEX

[76] Inventor: Robert N. Ammeraal, 11661 S. Nagle, Worth, Ill. 60482

[21] Appl. No.: 920,010

[22] Filed: Jul. 27, 1992

Related U.S. Application Data

[63] Continuation of Ser. No. 711,108, Jun. 4, 1991, abandoned, which is a continuation of Ser. No. 232,440, Aug. 15, 1988, abandoned.

[51] Int. Cl.$^5$ .................. A61K 31/705; A61K 31/715
[52] U.S. Cl. .......................................... 514/26; 514/58; 514/169; 514/177; 514/178; 536/5; 536/103
[58] Field of Search ............... 536/5, 103; 514/26, 514/58, 169, 177, 178

[56] References Cited

U.S. PATENT DOCUMENTS

| | | | |
|---|---|---|---|
| 4,303,787 | 12/1981 | Horikoshi et al. | 536/103 |
| 4,383,992 | 5/1983 | Lipari | 514/58 |
| 4,555,504 | 11/1985 | Jones | 514/26 |
| 4,596,795 | 6/1986 | Pitha | 514/58 |
| 4,668,626 | 5/1987 | Kobayashi et al. | 436/96 |
| 4,808,232 | 2/1989 | Beesley | 536/103 |
| 4,834,985 | 5/1989 | Elger et al. | 424/488 |
| 4,840,679 | 6/1989 | Ammeraal et al. | 536/103 |

FOREIGN PATENT DOCUMENTS

| | | |
|---|---|---|
| 327766 | 8/1989 | European Pat. Off. |
| 0220226 | 3/1985 | Fed. Rep. of Germany |
| 62-123196 | 6/1987 | Japan |
| 62-164701 | 7/1987 | Japan |
| 62-281855 | 12/1987 | Japan |
| 63-27440 | 2/1988 | Japan |
| 63-135402 | 6/1988 | Japan |
| 2109381 | 6/1983 | United Kingdom |
| 8502767 | 7/1985 | World Int. Prop. O. |

OTHER PUBLICATIONS

Szetli; Akademiai Klado, 1982, pp. 204-235.
Uekama et al; International Journal of Pharmaceutics 10:1-15 (1982).
Lopata et al; QSAR Strat Des. Bioact. Compd. Proc. Er, Symp. Quant. S. A. Relat. pp. 353-356 (1985).
Szetli; Starch 38(11): 388-390 (1986).
Kolzumi et al; Carbohydrate Research 153:55-67 (1986).
Koizumi et al; Chemical and Pharmaceutical Bulletin 35(8): 3413-3418 (Aug. 1987).
Koizumi et al; Chemical Abstracts 110:121385c (1989).
Yamamoto et al; International Journal of Pharmaceutics 49:163-171 (1989).
Taylor et al; Pharmaceutical Research 6(7) 641-646 (1989).

*Primary Examiner*—Johnnie R. Brown
*Assistant Examiner*—Nancy S. Carson
*Attorney, Agent, or Firm*—Lucas & Just

[57] ABSTRACT

A complex of branched beta cyclodextrin and steroid is formed by mixing a steroid and a branched beta cyclodextrin together in water for a period of about 4 to 24 hours under ambient conditions. The solubility of the steroid is increased about 95 times by employing the complex.

18 Claims, No Drawings

WATER SOLUBLE BRANCHED BETA CYCLODEXTRIN STEROID COMPLEX

This is a continuation of application Ser. No. 07/711,108 filed Jun. 4, 1991, now abandoned, which was a continuation of application Ser. No. 07/232,440 filed Aug. 15, 1988, also abandoned.

This invention relates to a complex of branched beta cyclodextrin and steroid and the use of such a complex to make the steroid water soluble.

Starch occurs naturally in a variety of plants such as corn, potato, sorghum and rice and is extracted from portions of the plant by a milling operation which separates the starch from the plant. Physically the starch is in a granular form which typically comprises both amylose and amylopectin. Amylose is a straight chained polymer of anhydroglucose units bonded together by alpha 1,4 bonds while amylopectin is a polymer composed of a straight chain of alpha 1,4 anhydroglucose onto which side chains of alpha 1,4 anhydroglucose polymers are bonded. In amylopectin, the bond between the straight chain and the side chain is an alpha 1,6 bond. The amount of amylose and amylopectin in a starch granule depends on the source of the starch. For example, high amylose corn starch contains about a 50:50 ratio while waxy corn starch contains about a 99:1 ratio of amylopectin to amylose.

Cyclodextrins, also called Schardingers dextrins, cycloamyloses, cyclomaltoses and cycloglucans, are polymers of anhydroglucose polymers, bonded together by alpha 1,4 bonds to form a ringed compound. A six membered ring is called alpha cyclodextrin, seven, beta cyclodextrin and eight, gamma cyclodextrin. These six, seven and eight membered rings are also referred to as cyclomaltohexaose, cyclomaltoheptaose and cyclomaltooctaose, respectively.

Branched cyclodextrins were described as early as 1965 by French and his co-workers, see French et al., "Archives of Biochem. and Biophys.", Volume III, 1965, pages 153-150, but had been studied very little until recently. Branched beta cyclodextrins, as their name implies, have one or more anhydroglucose units bonded onto the ring structure such that a branch extends out from the ring structure. The branch is bonded to the ring by an alpha 1,6 bond where the branched beta cyclodextrin is obtained from an enzymatic process.

Steroids are typically used in aqueous media and ointments as pharmaceutical preparations for treatment of the skin and eyes. Because steroids are highly water insoluble, any aqueous medium containing steroids must be vigorously shaken before application. Steroids are classified as lipids because they are highly water insoluble and are soluble in organic solvents.

In order to increase the water solubility of the steroid, it has been suggested in U.S. Pat. No. 4,383,992 issued May 17, 1983 that a complex of beta cyclodextrin and steroid be formed. It is alleged that such a complex is water soluble. Typically, a complex of a steroid and unsubstituted beta cyclodextrin contains less than about ½% soluble steroid at ambient conditions.

It has also been suggested that in order to increase the water solubility of a steroid a complex of alpha or gamma cyclodextrin and steroid be formed. Under ambient conditions, the alpha cyclodextrin-steroid solution typically contains less than about 1% soluble steroid and the gamma cyclodextrin-steroid solution also typically contains less than about 1% soluble steroid.

It has further been suggested that the beta cyclodextrin be chemically modified by reacting the beta cyclodextrin with methyl groups to form dimethyl beta cyclodextrin and then form a complex with a steroid. Such a chemically modified starch is not ideal for pharmaceutical use.

It has now been discovered that branched beta cyclodextrin will form a complex with a steroid and that such a complex is highly water soluble. In fact, it has been found that such a complex may have a solubility up to about 2800 times greater than that of the steroid itself and about 100 times greater than that of the complex of beta cyclodextrin and steroid.

These results are surprising because there had been speculation that the branch of anhydroglucose might interfere with or in some way react with the steroid itself and thus inhibit the complexation phenomenon between the steroid and the cavity of branched beta cyclodextrin. This is especially true for branched beta cyclodextrin where the branch length was greater than one anhydroglucose unit. Additionally, it is surprising that the complex of branched beta cyclodextrin and steroid has a solubility comparable to a complex of dimethyl-beta cyclodextrin and steroid. This is surprising because of the difference in chemical structure between the branched beta cyclodextrin and dimethyl-beta cyclodextrin.

Further, it is surprising that a complex forms between branched beta cyclodextrin and a steroid because of the hydrophillic nature of the branch itself and the hydrophobic nature of steroids.

Further, it is surprising that crystals of branched beta cyclodextrin and steroid were formed where the branch is one anhydroglucose unit because branched beta cyclodextrin having a branch of one anhydroglucose unit does not form a crystalline structure alone.

Branched beta cyclodextrins are conventionally prepared by treating starch slurry high in amylopectin with an enzyme, cyclodextrin glycosyltransferase (CGT), at the appropriate pH, temperature and time for the selected CGT. The starch used for this enzymatic preparation of branched beta cyclodextrin may be from any selected plant variety; however, it is preferable that the starch be high in amylopectin content. The enzyme CGT is obtained from microorganisms such as *Bacillus macerans, B. megaterium, B. circulans, B. stearothermophilus* and *Bacillus* sp. (alkalophilic) as well as others. Conventionally, the starch is slurried in aqueous solution at a concentration up to about 35% by weight solids. The slurry is then subjected to gelatinization and liquefaction by enzyme or acid to about 1 to about 5 DE. The preferred enzyme for liquefaction is bacterial alpha amylase. After deactivating the liquefying enzyme, the selected CGT is added to the gelatinized and liquefied slurry and the pH, temperature and time of the treatment are adjusted depending on the selected enzyme. Generally, the pH is between about 4.5 to about 8.5, the temperature ranges between ambient to about 75° C. and the length of the reaction runs for about ten hours to seven days. The amount of branched beta cyclodextrin will vary depending on the treatment conditions and the starch selected.

In order to produce predominantly beta cyclodextrin and branched beta cyclodextrin, the reaction between CGT and the gelatinized and liquefied starch slurry is conducted under a solvent such as toluene or p-xylene.

Such solvents substantially facilitate the isolation of branched beta cyclodextrin.

Normally, when starch is treated with CGT, branched beta cyclodextrins, beta cyclodextrins and other dextrins are formed. In order to obtain branched beta cyclodextrin, the branched beta cyclodextrin must be separated from the beta cyclodextrin and the other dextrins.

The purification and separation of branched beta cyclodextrin can be successfully accomplished by employing the method taught in U.S. Pat. No. 4,840,679 dated Jun. 20, 1989, which is incorporated by reference herein. As taught by that reference, branched beta cyclodextrin is separated from beta cyclodextrin and other dextrins by forming a first precipitate and a first liquor from an aqueous first solution containing . branched beta cyclodextrin by the addition of a beta cyclodextrin complexant to the aqueous first solution; recovering the first precipitate; forming a second aqueous solution with the first precipitate; forming a second precipitate and a second liquor from said second solution by the addition of a beta cyclodextrin complexant to said second solution; recovering the second liquor; and, finally, recovering branched beta cyclodextrin from said second liquor. The aqueous starting solution is an aqueous solution containing branched and non-branched beta cyclodextrins such that about 1% or more of the total solids content of the solution is branched beta cyclodextrin and such that the non-branched beta cyclodextrin is in an amount in excess of the branched beta cyclodextrin. Invariably, some beta cyclodextrin will be present with the branched beta cyclodextrin.

Branched beta cyclodextrins are characterized more specifically by the length of or the number of glucose units in the branch. For example, a branched beta cyclodextrin which has a single glucose unit attached to the ringed structure is called 6-alpha-D-glucosylcyclomaltoheptaose or GlcG7, a branched beta cyclodextrin having two glucose units on the branch is referred to as 6-alpha-D-maltosylcyclomaltoheptaose or G2cG7. A branched beta cyclodextrin with three glucose units on the branch is referred to conveniently as G3cG7, four glucose units as G4cG7, and so on.

The branched beta cyclodextrins may also be formed by a pyrolysis method, preferably as taught by the copending U.S. application Ser. No. 232,307, filed concurrently herewith now U.S. Pat. No. 5,007,967 issued Apr. 16, 1991. Such branched beta cyclodextrins have branches of anhydroglucose units which are bonded to the ring structure of the beta cyclodextrin by bonds other than a 1,6 bond. Branched beta cyclodextrin can also be formed by enzymatic techniques where anhydroglucose units are added onto the cyclodextrin ring, see for example U.S. Pat. No. 4,668,626 issued May 26, 1987. The term "branched beta cyclodextrin" as used in the specification and claims means branched beta cyclodextrin obtained from enzyme or pyrolysis.

Preferably, the branch length of the branched beta cyclodextrins used in the present invention is between about 1 to about 7 glucose units, i.e. GlcG7 to G7cG7. Good results have been obtained with GlcG7 to G3cG7.

It is thought that a complex forms between the steroid and the branched beta cyclodextrin where the steroid is a guest molecule inside the cavity of the branched beta cyclodextrin, which is acting as a host molecule. It is thought that not all of the steroid can physically fit inside the cavity of the branched beta cyclodextrin but that a portion of the polycyclic ring structure fits therein. Upon complexing with the branched beta cyclodextrin, the steroid, which is typically water insoluble, becomes highly water soluble.

Steroids which are suitable for complexing with branched beta cyclodextrins have a molecular structure which allows at least a portion of the steroid's molecular structure to be housed inside the cavity of the branched beta cyclodextrin. Suitable steroids include corticosteroids such as dexamethasone, prednisolone and hydrocortisone; androgens; anabolic steroids; estrogens; and progestogens. Good results have been obtained with hydrocortisone, progesterone and testosterone.

In order to form the complex between the branched beta cyclodextrin and the steroid, an aqueous mixture of steroid and branched beta cyclodextrin is prepared and gently mixed at ambient conditions. Stoichiometrically, the ratio of branched beta cyclodextrin to steroid is about 1:1; however, in order to complex as much of the steroid as possible, preferably an excess of branched beta cyclodextrin is added to the solution. Most preferably, the stoichiometric ratio of branched beta cyclodextrin to steroid is about 2:1, but this will vary with the individual steroid.

Preferably, first an aqueous solution of branched beta cyclodextrin is prepared such that the solution has a solids concentration of between about 10 to about 50% branched beta cyclodextrin based on the total weight of solution. Good results have been obtained when the aqueous solution of branched beta cyclodextrin has a solids concentration of about 14% by weight. This mixing is preferably carried out at ambient conditions. In order to prepare this solution, mixing can be employed. To this aqueous solution of branched beta cyclodextrin a steroid is added in the appropriate amount. The overall mixture of water, branched beta cyclodextrin and steroid is then gently mixed by conventional means while maintaining the mixture at ambient conditions. The mixing proceeds until an equilibrium is obtained, preferably for about 4 to about 24 hours.

The complex of branched beta cyclodextrin and steroid is then obtained from the aqueous solution in a conventional manner, typically by evaporation. Alternatively, the complex is left in solution and merely concentrated or evaporated to the appropriate concentration for use. Crystals of GlcG7 and hydrocortisone may be obtained by concentration to about 30% solids. Upon cooling and standing at 30% solids the complex crystallizes from solution. The material obtained from drying is an equilibrium mixture of complex, free branched beta cyclodextrin and a trace of free steroid. If crystals are obtained, as is the case with GlcG7 and hydrocortisone, subsequent solutions of the crystalline complex in water may result in precipitation of free steroid unless an appropriate amount of free branched beta cyclodextrin is present.

Incorporation of the steroid-branched beta cyclodextrin complex in a pharmaceutical preparation is accomplished in a conventional manner. However, because of the increased solubility of the complex, the steroid can more readily be incorporated into a pharmaceutical preparation.

These and other aspects of the present invention may be more fully understood by reference to the following examples.

EXAMPLE 1

This example illustrates preparation of a complex of branched beta cyclodextrin and steroid where the steroid is hydrocortisone.

A solution of branched beta cyclodextrin was prepared to about 14% solids by adding branched beta cyclodextrin to water in the amounts shown below in Table 1. To this solution was added the hydrocortisone in the amounts shown in Table 1 below. The mixture was stirred for about 4 hours and then filtered to remove undissolved hydrocortisone. The filtrate contained the complex, the free branched beta cyclodextrin and trace free hydrocortisone. This example was run at ambient conditions. Table 1 below further illustrates this example.

TABLE 1

| Element | Amount (gm) |
| --- | --- |
| Carbohydrate added | 1.390 |
| Free branched beta cyclodextrin added | 1.370 |
| Free branched beta cyclodextrin after complexation | .413 |
| Average molecular weight of branched beta cyclodextrin = | 1328 |
| Average DP of branch = | 1.19 |
| Hydrocortisone complexed in branched beta cyclodextrin | .250 |
| Free beta cyclodextrin added (impurity) | .083 |
| Free beta cyclodextrin after complexation | .025 |
| Complexed beta cyclodextrin | .058 |
| Hydrocortisone complexed in beta cyclodextrin | .019 |
| Free hydrocortisone added | .400 |
| Free soluble hydrocortisone after complexation | .002 |
| Insoluble hydrocortisone after complexation | .129 |
| Complexation hydrocortisone (.271 − 002) = | .269 |
| $\left( S = \frac{271}{9.46} = 28.65; So = .36 \text{ mg/ml} \right)$ | |
| S/So = | 79.57 |
| Water = | 8.54 ml |
| Solution = | 9.46 ml |
| Total Weight of Complex | 1.243 |
| Total Weight Hydrocortisone:Branched beta cyclodextrin | 1.166 |
| Total Weight Hydrocortisone:Beta cyclodextrin | .077 |
| Efficiency (assume 1:1 complex) .916/1.307 = | .7008 |

The hydrocortisone was a commercially available hydrocortisone having a high purity.

The amount of carbohydrate added, free steroid added, and water were measured using a conventional analytical balance. Chromatographic procedures were used to determine the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The branched beta cyclodextrin was obtained by solvent precipitation and chromatographic separation from a typical CGT digest of 5 DE waxy hydrolysate. The beta cyclodextrin and other carbohydrates which are not branched beta cyclodextrin are impurities which were not fully separated.

The solubility of hydrocortisone in water under ambient conditions has been reported as 0.36 mg/ml. The observed solubility in water of the branched beta cyclodextrin and hydrocortisone complex in this example after concentration was 65.0 mg/ml under ambient conditions. By employing the present invention the solubility of the steroid has been increased by a factor of 181.

EXAMPLE 2

This example illustrates preparation of a complex of branched beta cyclodextrin and steroid where the steroid is hydrocortisone.

A solution of branched beta cyclodextrin was prepared to about 14% solids by adding branched beta cyclodextrin to water in the amounts shown below in Table 2. To this solution was added the hydrocortisone in the amounts shown in Table 2 below. The mixture was stirred for about 20 hours and then filtered to remove undissolved hydrocortisone. The filtrate contained the complex, the free branched beta cyclodextrin and trace free hydrocortisone. This example was run at ambient conditions. Table 2 below further illustrates this example.

TABLE 2

| Element | Amount (gm) |
| --- | --- |
| Carbohydrate added | 1.400 |
| Free branched beta cyclodextrin added | 1.202 |
| Free branched beta cyclodextrin after complexation | .361 |
| Complexed branched beta cyclodextrin | .841 |
| Average molecular weight of branched beta cyclodextrin = | 1828 |
| Average DP of branch = | 4.27 |
| Hydrocortisone complexed in branched beta cyclodextrin | .167 |
| Free beta cyclodextrin added (impurity) | — |
| Free beta cyclodextrin after complexation | — |
| Complexed beta cyclodextrin | — |
| Hydrocortisone complexed in beta cyclodextrin | — |
| Free hydrocortisone added | .2986 |
| Free soluble hydrocortisone after complexation | .0031 |
| Insoluble hydrocortisone after complexation | .1286 |
| Complexation hydrocortisone (.1700 − .0031) = | .1669 |
| $\left( S = \frac{170}{9.52} = 17.86; So = .36 \text{ mg/ml} \right)$ | |
| S/So = | 49.60 |
| Water = | 8.6 ml |
| Solution = | 9.52 ml |
| Total Weight of Complex | 1.008 |
| Total Weight Hydrocortisone:Branched beta cyclodextrin | 1.008 |
| Total Weight Hydrocortisone:Beta cyclodextrin | — |

The hydrocortisone was a commercially available hydrocortisone having a high purity.

The amount of carbohydrate added, free steroid added, and water were measured using a conventional analytical balance. Chromatographic procedures were used to determine the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The branched beta cyclodextrin was obtained by solvent precipitation and chromatographic separation from a typical CGT digest of 5 DE waxy hydrolysate. The beta cyclodextrin and other carbohydrates which are not branched beta cyclodextrin are impurities which were not fully separated.

The solubility of hydrocortisone in water under ambient conditions has been reported as 0.36 mg/ml. The observed solubility in water of the branched beta cyclodextrin and hydrocortisone complex in this example after concentration was 21.4 mg/ml under ambient conditions. By employing the present invention the solubility of the steroid has been increased by a factor of 59.

EXAMPLE 3

This example illustrates preparation of a complex of branched beta cyclodextrin and steroid where the steroid is progesterone.

A solution of branched beta cyclodextrin was prepared to about 14% solids by adding branched beta cyclodextrin to water in the amounts shown below in Table 3. To this solution was added the progesterone in the amounts shown in Table 3 below. The mixture was stirred for about 20 hours and then filtered to remove undissolved progesterone. The filtrate contained the complex, the free branched beta cyclodextrin and trace free progesterone. This example was run at ambient conditions. Table 3 below further illustrates this example.

TABLE 3

| Element | Amount (gm) |
| --- | --- |
| Carbohydrate added | 1.400 |
| Free branched beta cyclodextrin added | 1.202 |
| Free branched beta cyclodextrin after complexation | .677 |
| Complexed branched beta cyclodextrin | .525 |
| Average molecular weight of branched beta cyclodextrin = | 1828 |
| Average DP of branch = | 4.27 |
| Progesterone complexed in branched beta cyclodextrin | .0904 |
| Free beta cyclodextrin added (impurity) | — |
| Free beta cyclodextrin after complexation | — |
| Complexed beta cyclodextrin | — |
| Progesterone complexed in beta cyclodextrin | — |
| Free progesterone added | .3000 |
| Free soluble progesterone after complexation | .00014 |
| Insoluble progesterone after complexation | .2095 |
| Complexation progesterone (.0905 − .0001) = | .0904 |

$$\left( S = \frac{90.4}{9.52} = 9.50; So = .016 \text{ mg/ml} \right)$$

| | |
| --- | --- |
| S/So = | 593.5 |
| Water = | 8.6 ml |
| Solution = | 9.52 ml |
| Total Weight of Complex | .615 |
| Total Weight Progesterone:Branched beta cyclodextrin | .615 |
| Total Weight Progesterone:Beta cyclodextrin | — |
| Efficiency (complexed/total branched beta cyclodextrin) | .437 |

The progesterone was a commercially available progesterone having a high purity.

The amount of carbohydrate added, free steroid added, and water were measured using a conventional analytical balance. Chromatographic procedures were used to determine the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The branched beta cyclodextrin was obtained by solvent precipitation and chromatographic separation from a typical CGT digest of 5 DE waxy hydrolysate. The beta cyclodextrin and other carbohydrates which are not branched beta cyclodextrin are impurities which were not fully separated.

The solubility of progesterone in water under ambient conditions has been reported as 0.016 mg/ml. The observed solubility in water of the branched beta cyclodextrin and progesterone complex in this example after concentration was 44.8 mg/ml under ambient conditions. By employing the present invention the solubility of the steroid has been increased by a factor of 2800.

EXAMPLE 4

This example illustrates preparation of a complex of branched beta cyclodextrin and steroid where the steroid is testosterone.

A solution of branched beta cyclodextrin was prepared to about 14% solids by adding branched beta cyclodextrin to water in the amounts shown below in Table 4. To this solution was added the testosterone in the amounts shown in Table 4 below. The mixture was stirred for about 20 hours and then filtered to remove undissolved testosterone. The filtrate contained the complex, the free branched beta cyclodextrin and trace free testosterone. This example was run at ambient conditions. Table 4 below further illustrates this example.

TABLE 4

| Element | Amount (gm) |
| --- | --- |
| Carbohydrate added | 1.400 |
| Free branched beta cyclodextrin added | 1.202 |
| Free branched beta cyclodextrin after complexation | .644 |
| Complexed branched beta cyclodextrin | .558 |
| Average molecular weight of branched beta cyclodextrin = | 1828 |
| Average DP of branch = | 4.27 |
| Testosterone complexed in branched beta cyclodextrin | .088 |
| Free beta cyclodextrin added (impurity) | — |
| Free beta cyclodextrin after complexation | — |
| Complexed beta cyclodextrin | — |
| Testosterone complexed in beta cyclodextrin | — |
| Free testosterone added | .303 |
| Free soluble testosterone after complexation | .00034 |
| Insoluble testosterone after complexation | .215 |
| Complexation testosterone (.088 = .000) = | .088 |

$$\left( S = \frac{88}{9.52} = 9.24; So = 0.40 \text{ mg/ml} \right)$$

| | |
| --- | --- |
| S/So = | 231.1 |
| Water = | 8.6 ml |
| Solution = | 9.52 ml |
| Total Weight of Complex | .646 |
| Total Weight Testosterone:Branched beta cyclodextrin | .646 |
| Total Weight Testosterone:Beta cyclodextrin | — |
| Efficiency Complexed:Total Branched beta cyclodextrin = | .464 |

The testosterone was a commercially available testosterone having a high purity.

The amount of carbohydrate added, free steroid added, and water were measured using a conventional analytical balance. Chromatographic procedures were used to determine the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The branched beta cyclodextrin was obtained by solvent precipitation and chromatographic separation from a typical CGT digest of 5 DE waxy hydrolysate. The beta cyclodextrin and other carbohydrates which are not branched beta cyclodextrin are impurities which were not fully separated.

The solubility of testosterone in water under ambient conditions has been reported as 0.040 mg/ml. The observed solubility in water of the branched beta cyclodextrin and testosterone complex in this example after concentration was 39.8 mg/ml under ambient conditions. By employing the present invention the solubility of the steroid has been increased by a factor of 995.

EXAMPLE 5

This example illustrates preparation of a complex of branched beta cyclodextrin and steroid where the steroid is hydrocortisone.

A solution of branched beta cyclodextrin was prepared to about 14% solids by adding branched beta cyclodextrin to water in the amounts shown below in Table 5. To this solution was added the hydrocortisone in the amounts shown in Table 5 below. The mixture was stirred for about 21 hours and then filtered to remove undissolved hydrocortisone. The filtrate contained the complex, the free branched beta cyclodextrin and trace free hydrocortisone. This example was run at ambient conditions. Table 5 below illustrates this example.

TABLE 5

| Element | Amount (gm) |
| --- | --- |
| Carbohydrate added | 1.970 |
| Free branched beta cyclodextrin added | 1.604 |
| Free branched beta cyclodextrin after complexation | .481 |
| Complexed branched beta cyclodextrin | 1.123 |
| Average molecular weight of branched beta cyclodextrin = | 1867 |
| Average DP of branch = | 4.52 |
| Hydrocortisone complexed in branched beta cyclodextrin | .218 |
| Free beta cyclodextrin addded (impurity) | .090 |
| Free beta cyclodextrin after complexation | .023 |
| Complexed beta cyclodextrin | .071 |
| Hydrocortisone complexed in beta cyclodextrin | .023 |
| Free hydrocortisone added | .545 |
| Free soluble hydrocortisone after complexation | .0044 |
| Insoluble hydrocortisone after complexation | .299 |
| Complexation hydrocortisone (.246 − .0004) = | .242 |

$$\left(S = \frac{246}{13.40} = 18.36; So = 0.36 \text{ mg/ml}\right)$$

| | |
| --- | --- |
| S/So = | 51.00 |
| Water = | 12.101 ml |
| Solution = | 13.40 ml |

TABLE 5-continued

| Element | Amount (gm) |
| --- | --- |
| Total Weight of Complex | 1.435 |
| Total Weight Hydrocortisone:Branched beta cyclodextrin | 1.341 |
| Total Weight Hydrocortisone:Beta cyclodextrin | .094 |

The branched beta cyclodextrin was isolated from pyrolyzed branched beta cyclodextrin by solvent precipitation and chromatographic separation.

The hydrocortisone was a commercially available hydrocortisone having a high purity.

The amount of carbohydrate added, free steroid added, and water were measured using a conventional analytical balance. Chromatographic procedures were used to determine the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The solubility of hydrocortisone in water under ambient conditions has been reported as 0.36 mg/ml. The observed solubility in water of the branched beta oyclodextrin and hydrocortisone complex in this example after concentration was 87.1 mg/ml under ambient conditions. By employing the present invention the solubility of the steroid has been increased by a factor of 242.

EXAMPLE 6

This example illustrates preparation of a complex of branched beta cyclodextrin and steroid where the steroid is hydrocortisone.

A solution of branched beta cyclodextrin was prepared to about 14% solids by adding branched beta cyclodextrin to water in the amounts shown below in Table 6. To this solution was added the hydrocortisone in the amounts shown in Table 6 below. The mixture was stirred for about 4 hours and then filtered to remove undissolved hydrocortisone. The filtrate contained the complex, the free branched beta cyclodextrin and trace free hydrocortisone. This example was run at ambient conditions. Table 6 below further illustrates this example.

TABLE 6

| Element | Amount (gm) |
| --- | --- |
| Carbohydrate added | 1.670 |
| Free branched beta cyclodextrin added | 1.635 |
| Free branched beta cyclodextrin after complexation | .489 |
| Complexed branched beta cyclodextrin | 1.146 |
| Average molecular weight of branched beta cyclodextrin = | 4035 |
| Average DP of branch = | 17.9 |
| Hydrocortisone complexed in branched beta cyclodextrin | .103 |
| Free beta cyclodextrin added (impurity) | — |
| Free beta cyclodextrin after complexation | — |
| Complexed beta cyclodextrin | — |
| Hydrocortisone complexed in beta cyclodextrin | — |
| Free hydrocortisone added | .150 |
| Free soluble hydrocortisone after complexation | .004 |
| Insoluble hydrocortisone after complexation | .043 |
| Complexation hydrocortisone (.107 − .004) = | .103 |

TABLE 6-continued

| Element | Amount (gm) |
| --- | --- |
| $\left(S = \frac{107}{11.4} = 9.39; So - .36 \text{ mg/ml}\right)$ | |
| S/So = | 26.07 |
| Water = | 10.3 ml |
| Solution = | 11.4 ml |
| Total Weight of Complex | 1.249 |
| Total Weight Hydrocortisone:Branched beta cyclodextrin | 1.249 |
| Total Weight Hydrocortisone:Beta cyclodextrin | — |
| Efficiency (assume 1:1 complex) 1.146/1.635 = | .7009 |

The hydrocortisone was a commercially available hydrocortisone having a high purity.

The amount of carbohydrate added, free steroid added, and water were measured using a conventional analytical balance. Chromatographic procedures were used to determine the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The branched beta cyclodextrin was obtained by solvent precipitation and chromatographic separation from a typical CGT digest of 5 DE waxy hydrolysate. The beta cyclodextrin and other carbohydrates which are not branched beta cyclodextrin are impurities which were not fully separated.

The solubility of hydrocortisone in water under ambient conditions has been reported as 0.36 mg/ml. The observed solubility in water of the branched beta cyclodextrin and hydrocortisone complex in this example after concentration was 53.6 mg/ml under ambient conditions. By employing the present invention the solubility of the steroid has been increased by a factor of 149.

EXAMPLE 7

This example illustrates preparation of a complex of branched beta cyclodextrin and steroid where the steroid is cholesterol.

A solution of branched beta cyclodextrin was prepared to about 14% solids by adding branched beta cyclodextrin to water in the amounts shown below in Table 7. To this solution was added the cholesterol in the amounts shown in Table 7 below. The mixture was stirred for about 20 hours and then filtered to remove undissolved cholesterol. The filtrate contained the complex, the free branched beta cyclodextrin and trace free cholesterol. This example was run at ambient conditions. Table 7 below further illustrates this example.

TABLE 7

| Element | Amount (gm) |
| --- | --- |
| Carbohydrate added | 1.400 |
| Free branched beta cyclodextrin added | 1.202 |
| Free branched beta cyclodextrin after complexation | 1.037 |
| Complexed branched beta cyclodextrin | .165 |
| Average molecular weight of branched beta cyclodextrin = | 1828 |
| Average DP of branch = | 4.27 |
| Cholesterol complexed in branched beta cyclodextrin | .035 |
| Free beta cyclodextrin added (impurity) | — |
| Free beta cyclodextrin after complexation | — |
| Complexed beta cyclodextrin | — |
| Cholesterol complexed in beta cyclodextrin | — |
| Free cholesterol added | .300 |
| Free soluble cholesterol after complexation | .00002 |
| Insoluble cholesterol after complexation | .265 |
| Complexation cholesterol (.035 − .000) = | .035 |
| $\left(S = \frac{35}{9.52} = 3.68; So - .002 \text{ mg/ml}\right)$ | |
| S/So = | 183.8 |
| Water = | 8.6 ml |
| Solution = | 9.52 ml |
| Total Weight of Complex | .200 |
| Total Weight Cholesterol:Branched beta cyclodextrin | .200 |
| Total Weight Cholesterol:Beta cyclodextrin | — |
| Efficiency = | .137 |

The cholesterol was a commercially available cholesterol having a high purity.

The amount of carbohydrate added, free steroid added, and water were measured using a conventional analytical balance. Chromatographic procedures were used to determined the percentages of branched beta cyclodextrin, beta cyclodextrin and other carbohydrates present in the carbohydrates added. The amount of insoluble steroid after complexation was determined by the difference between the dry weight of the filter paper before filtration and the dry weight of the filter paper after washing to remove excess carbohydrate and drying. The remaining values in the table above were calculated.

The branched beta cyclodextrin was obtained by solvent precipitation and chromatographic separation from a typical CGT digest of 5 DE waxy hydrolysate. The beta cyclodextrin and other carbohydrates which are not branched beta cyclodextrin are impurities which were not fully separated.

The solubility of cholesterol in water under ambient conditions has been reported as 0.002 mg/ml. The observed solubility in water of the branched beta cyclodextrin and cholesterol complex in this example was 3.7 mg/ml under ambient conditions. By employing the present invention the solubility of the steroid has been increased by a factor of 1838.

EXAMPLE 8

This example compares the solubility of the branched beta cyclodextrin-steroid complex of the present invention against like steroids complexed with gamma cyclodextrin, alpha cyclodextrin, beta cyclodextrin, and dimethyl beta cyclodextrin. The gamma, alpha, and dimethyl beta cyclodextrin complexes were prepared under ambient conditions with cyclodextrins at a concentration of 0.075M. Because of the low solubility of beta cyclodextrin the concentration of this solution was 0.0112M in water under ambient conditions. The results of this example are reported in Table 8 below.

TABLE 8

| | Methyltestosterone[a] Testosterone[b] | Solubility (mg/ml) | |
| --- | --- | --- | --- |
| | | Progesterone | Hydrocortisone |
| Present Invention | 10.03[b] (Example 4) | 10.32 (Example 3) | 20.66 (Example 1) |
| Dimethyl Beta Cyclodextrin | 13.70[a] | 13.00 | 20.30 |
| Gamma Cyclodextrin | 1.40[a] | 0.09 | 4.30 |
| Alpha Cyclodextrin | 0.43[a] | 0.27 | 3.80 |
| Beta Cyclodextrin | 0.19[a] | 0.09 | 1.82 |

Clearly the present invention produces superior results compared to the gamma and beta cyclodextrin and comparable results to dimethyl beta cyclodextrin.

The values of the dimethyl beta, gamma and alpha cyclodextrin steroid complex were taken from reported data.

The values of the present invention reported above were calculated from Examples 1, 3, and 4 above for comparative purposes.

It will be understood that the preferred embodiments of the present invention herein chosen for the purpose of illustration are intended to cover all changes and modifications of the preferred embodiments of the present invention which do not constitute a departure from the spirit and scope of the present invention.

What is claimed is:

1. A water soluble compound formed by complexing branched beta cyclodextrins with a steroid, said branched beta cyclodextrins being a non-uniform mix of branched beta cyclodextrin of varying branch length with an average degree of polymerization selected from the group consisting of 4.27, 4.54 and 17.9, said steroid having a molecular structure that can fit into the cavity of the branched beta cyclodextrin and form a complex with the branched beta cyclodextrin.

2. The water soluble compound of claim 1 wherein the steroid is selected from the group consisting of: corticosteroids, androgens, anabolic steroids, estrogens, and progestogens; that have a molecular structure that can fit into the cavity of the branched beta cyclodextrin and form a complex with the branched beta cyclodextrin.

3. The water soluble compound of claim 1 wherein the steroid is selected from the group consisting of: dexamethasone, prednisolone and cholesterol.

4. The water soluble compound of claim 1 wherein the branched beta cyclodextrin has a branch containing between about 4 glucose units to about 7 glucose units.

5. The water soluble compound of claim 3 wherein the branched beta cyclodextrin has a branch containing between about 4 glucose units to about 7 glucose units.

6. A method for increasing the solubility of a steroid comprising the steps of:

(a) forming an aqueous mixture of branched beta cyclodextrins and a steroid in a stoichiometric ratio of about 1:1, said branched beta cyclodextrins being a non-uniform mix of branched beta cyclodextrin of varying branch length with an average degree of polymerization selected from the group consisting of 4.27, 4.52 and 17.9, said steroid having a molecular structure that can fit into the cavity of the branched beta cyclodextrin and form a complex with the branched beta cyclodextrin; and (b) recovering a complex of branched beta cyclodextrin and steroid.

7. The method of claim 6 wherein the formation of the aqueous mixture of branched beta cyclodextrin and steroid is conducted under ambient conditions.

8. The method of claim 6 wherein the formation step is accomplished by adding branched beta cyclodextrin to water and then adding the steroid and mixing the branched beta cyclodextrin and steroid in water for a period of about 4 to about 24 hours under ambient conditions.

9. The method of claim 6 wherein the recovery step is accomplished by evaporation.

10. The method of claim 8 wherein the recovery step is accomplished by evaporation.

11. The water soluble compound of claim 1 wherein the average branch length is about 4.27 glucose units.

12. The water soluble compound of claim 1 wherein the average branch length is about 4.52 glucose units.

13. The water soluble compound of claim 1 wherein the average branch length is about 17.9 glucose units.

14. The water soluble compound of claim 11 wherein the steroid is selected from the group consisting of: corticosteroids, androgens, anabolic steroids, estrogens, and progestogens; that have a molecular structure that can fit into the cavity of the branched beta cyclodextrin and form a complex with the branched beta cyclodextrin.

15. The water soluble compound of claim 12 wherein the steroid is selected from the group consisting of: corticosteroids, androgens, anagolic steroids, estrogens, and progestogens; that have a molecular structure that can fit into the cavity of the branched beta cyclodextrin and form a complex with the branched beta cyclodextrin.

16. The water soluble compound of claim 13 wherein the steroid is selected from the group consisting of: corticosteroids, androgens, anabolic steroids, estrogens, and progestogens; that have a molecular structure that can fit into the cavity of the branched beta cyclodextrin and form a complex with the branched beta cyclodextrin.

17. The water soluble compound of claim 1 wherein the branches of the cyclodextrin have an average degree of polymerization selected from the group consisting of 4.27, 4.52 and 17.9

18. The water soluble compound of claim 17 wherein the steroid is selected from the group consisting of: corticosteroids, androgens, anabolic steroids, estrogens, and progestogens; that have a molecular structure that can fit into the cavity of the branched beta cyclodextrin and form a complex with the branched beta cyclodextrin.

* * * * *

UNITED STATES PATENT AND TRADEMARK OFFICE
CERTIFICATE OF CORRECTION

PATENT NO. : 5,229,370
DATED : July 20, 1993
INVENTOR(S) : Robert N. Ammeraal et al.

It is certified that error appears in the above-identified patent and that said Letters Patent is hereby corrected as shown below:

Column 3, line 16, delete ".".

Column 5, line 21 (Table 1), change "1.370" to --1.307--.

Column 5, between lines 23 and 24 (Table 1), insert:
 --Complexed branched beta cyclodextrin   .916--

Column 9, line 62 (Table 5), change ".0004" to --.004--.

Column 10, lines 29-30, change "oyclodextrin" to --cyclodextrin--.

Column 13, line 36 (claim 1), change "4.54" to --4.52--.

Column 14, line 38 (claim 15), change "anagolic" to --anabolic--.

Column 14, line 53 (claim 17), after "17.9" insert --.--.

Signed and Sealed this

Fifteenth Day of March, 1994

Attest:

BRUCE LEHMAN

Attesting Officer   Commissioner of Patents and Trademarks